United States Patent
Weihe et al.

(10) Patent No.: US 10,441,340 B2
(45) Date of Patent: Oct. 15, 2019

(54) SURGICAL FORCEPS

(71) Applicant: COVIDIEN LP, Mansfield, MA (US)

(72) Inventors: Jason G. Weihe, Longmont, CO (US);
William E. Robinson, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 400 days.

(21) Appl. No.: 14/722,514

(22) Filed: May 27, 2015

(65) Prior Publication Data
US 2016/0345992 A1 Dec. 1, 2016

(51) Int. Cl.
A61B 17/28 (2006.01)
A61B 18/08 (2006.01)
A61B 17/29 (2006.01)
A61B 18/14 (2006.01)
A61B 34/30 (2016.01)

(52) U.S. Cl.
CPC ............ *A61B 18/085* (2013.01); *A61B 17/29* (2013.01); *A61B 18/1445* (2013.01); *A61B 34/30* (2016.02); *A61B 2017/2934* (2013.01); *A61B 2017/2937* (2013.01)

(58) Field of Classification Search
CPC ..... A61B 17/29; A61B 18/00; A61B 18/1445; A61B 2017/2934; A61B 2017/2936; A61B 2017/2937
See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |

(Continued)

FOREIGN PATENT DOCUMENTS

| CN | 201299462 | 9/2009 |
| DE | 2415263 A1 | 10/1975 |

(Continued)

OTHER PUBLICATIONS

U.S. Appl. No. 14/098,953, filed Dec. 6, 2013; inventor: Cunningham.

(Continued)

*Primary Examiner* — Daniel W Fowler
*Assistant Examiner* — Tigist S Demie

(57) ABSTRACT

A forceps includes an end effector assembly having first and second jaw members each defining a proximal portion, a distal portion, and an intermediate portion. The distal portions define tissue-treating surfaces and the intermediate portions are disposed in overlapping relation relative to one another. A shaft is configured to receive the proximal portions and includes a retention feature for operably retaining the first and second jaw members at the distal end of the shaft. A drive bar is disposed within the shaft and operably associated with the proximal portions such that translation of the drive bar through the shaft and relative to the end effector assembly moves the first and second jaw members between a spaced-apart position and an approximated position for grasping tissue between the tissue-treating surfaces thereof.

8 Claims, 4 Drawing Sheets

(56) References Cited

U.S. PATENT DOCUMENTS

| | | |
|---|---|---|
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,709,680 A | 1/1998 | Yates et al. |
| H1745 H | 4/1998 | Paraschac |
| D402,028 S | 12/1998 | Grimm et al. |
| D408,018 S | 4/1999 | McNaughton |
| 5,922,002 A | 7/1999 | Yoon |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,554,829 B2 | 4/2003 | Schulze et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,628,792 B2 | 12/2009 | Guerra |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,837,631 B2 | 11/2010 | Diamond et al. |
| D630,324 S | 1/2011 | Reschke |
| 7,935,052 B2 | 5/2011 | Dumbauld |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| 8,382,792 B2 | 2/2013 | Chojin |
| D680,220 S | 4/2013 | Rachlin |
| 8,491,625 B2 | 7/2013 | Horner |
| 8,585,736 B2 | 11/2013 | Horner et al. |
| 8,636,761 B2 | 1/2014 | Cunningham et al. |
| 2011/0295314 A1 | 12/2011 | Staud |
| 2012/0101484 A1* | 4/2012 | Miersch ............... A61B 17/29 606/1 |
| 2012/0130367 A1* | 5/2012 | Garrison ............... A61B 17/29 606/41 |
| 2013/0085516 A1* | 4/2013 | Kerr .................... A61B 18/1442 606/167 |
| 2014/0025070 A1 | 1/2014 | Kerr et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |

(56) References Cited

FOREIGN PATENT DOCUMENTS

| JP | 2005-152663 A | 6/2005 |
|---|---|---|
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999. (1 page).
Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/ Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.
U.S. Appl. No. 14/065,644, filed Oct. 29, 2013; inventor: Reschke.

\* cited by examiner

SURGICAL FORCEPS

BACKGROUND

Technical Field

The present disclosure relates to surgical instruments and, more particularly, to surgical forceps configured for treating tissue.

Background of Related Art

A surgical forceps is a plier-like device which relies on mechanical action between its jaws to grasp, clamp, and constrict tissue. Energy-based surgical forceps utilize both mechanical clamping action and energy to treat, e.g., coagulate, cauterize, and/or seal, tissue.

Generally, surgical instruments, including surgical forceps, can be classified as disposable instruments, e.g., instruments that are discarded after a single use, or reusable instruments, e.g., instruments capable of being sterilized for repeated use. As can be appreciated, those instruments that are configured for single-use must be cost-efficient while still being capable of effectively performing their intended functions.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A forceps provided in accordance with aspects of the present disclosure includes an end effector assembly having first and second jaw members each defining a proximal portion, a distal portion, and an intermediate portion extending between and interconnecting the respective proximal and distal portions. The distal portions of the first and second jaw members defines tissue-treating surfaces configured to grasp tissue therebetween. The intermediate portions of the first and second jaw members are disposed in overlapping relation relative to one another. A shaft defining a proximal end and a distal end is configured to receive the proximal portions of the first and second jaw members within the distal end thereof. The distal portions of the first and second jaw members are configured to extend distally from the distal end of the shaft. The shaft defines a retention feature at the distal end thereof that is configured to receive the intermediate portions of the first and second jaw members therethrough and inhibit passage of the proximal and distal portions of the first and second jaw members therethrough, thereby operably retaining the first and second jaw members at the distal end of the shaft. A drive bar disposed within the shaft is operably associated with the proximal portions of the first and second jaw members such that translation of the drive bar through the shaft and relative to the end effector assembly moves the first and second jaw members between a spaced-apart position and an approximated position for grasping tissue between the tissue-treating surfaces thereof.

In an aspect of the present disclosure, the first and second jaw members define camming surfaces and the drive bar is configured to cam along the camming surfaces to move the first and second jaw members from the spaced-apart position to the approximated position. Further, the drive bar may include a hollow distal end defining an interior annular surface. In such aspects, the drive bar is configured for advancement about the proximal portions of the first and second jaw members such that the interior annular surface cams about the camming surfaces to move the first and second jaw members from the spaced-apart position to the approximated position.

In another aspect of the present disclosure, a biasing member is disposed between the proximal portions of the first and second jaw members. The biasing member is configured to bias the first and second jaw members towards the spaced-apart position.

In yet another aspect of the present disclosure, the retention feature is an annular flange defining a reduced opening at the distal end of the shaft. The reduced opening has a diameter greater than that of the intermediate portions of the first and second jaw members and less than that of the proximal and distal portions of the first and second jaw members.

In still another aspect of the present disclosure, one or both of the tissue-treating surfaces is adapted to connect to a source or energy for treating tissue grasped therebetween.

In still yet another aspect of the present disclosure, a housing is supported at the proximal end of the shaft and a handle assembly is associated with the housing. The handle assembly includes a movable handle coupled to the drive bar. The movable handle is selectively actuatable for translating the drive bar through the shaft and relative to the end effector assembly.

In another aspect of the present disclosure, the drive bar is configured to move the proximal portions of the first and second jaw members towards one another to thereby move the first and second jaw members from the spaced-apart position to the approximated position.

Another forceps provided in accordance with aspects of the present disclosure includes an end effector assembly having first and second jaw members each defining a proximal portion and a distal portion. The proximal portions of the first and second jaw members are inter-fit with one another at two intersection areas so as to retain the proximal portions in substantially fixed position and orientation relative to one another. The distal portions of the first and second jaw members define tissue-treating surfaces. The first and second jaw members are configured to move relative to one another between a spaced-apart position and an approximated position for grasping tissue between the tissue-treating surfaces. A drive assembly operably associated with the end effector assembly includes a fixed drive bar and a movable drive bar. The fixed drive bar is configured to retain the proximal portions of the first and second jaw members therein, while the movable drive bar is movable relative to the fixed drive bar and the first and second jaw members for moving the first and second jaw members from the spaced-apart position to the approximated position for grasping tissue between the tissue-treating surfaces thereof.

In an aspect of the present disclosure, the first and second jaw members are configured to flex relative to one another intermediate the proximal and distal portions thereof for moving the first and second jaw members from the spaced-apart position to the approximated position.

In another aspect of the present disclosure, the distal portions of the first and second jaw members define camming surfaces and the movable drive bar is configured to cam along the camming surfaces to move the first and second jaw members from the spaced-apart position to the approximated position.

In still another aspect of the present disclosure, the movable drive bar is slidably disposed about the fixed drive bar and the end effector assembly and is configured to cam about the distal portions of the first and second jaw members to move the first and second jaw members from the spaced-apart position to the approximated position.

In yet another aspect of the present disclosure, a fixed outer shaft is disposed about the movable drive bar.

In still yet another aspect of the present disclosure, a housing is supported at the proximal end of the fixed outer shaft and a handle assembly is associated with the housing. The handle assembly includes a movable handle coupled to the movable drive bar that is selectively actuatable for translating the movable drive bar through the fixed outer shaft and relative to the fixed drive bar and the end effector assembly.

In another aspect of the present disclosure, the proximal portions of the first and second jaw members define arcuate configurations of opposite orientation such that the proximal portions intersect one another at each of the intersection areas.

In another aspect of the present disclosure, at each of the intersection areas, one of the proximal portions includes a recess and the other of the proximal portions includes a complementary protrusion configured for receipt with the corresponding recess to inter-fit the proximal portions with one another.

In yet another aspect of the present disclosure, the fixed drive bar includes one or more retention structures disposed therein for retaining the proximal portions of the first and second jaw members therein.

In still another aspect of the present disclosure, one or both of the tissue-treating surfaces is adapted to connect to a source or energy for treating tissue grasped therebetween.

BRIEF DESCRIPTION OF THE DRAWINGS

Various aspects and features of the present disclosure described herein with reference to the drawings wherein.

DETAILED DESCRIPTION

Figure 1:
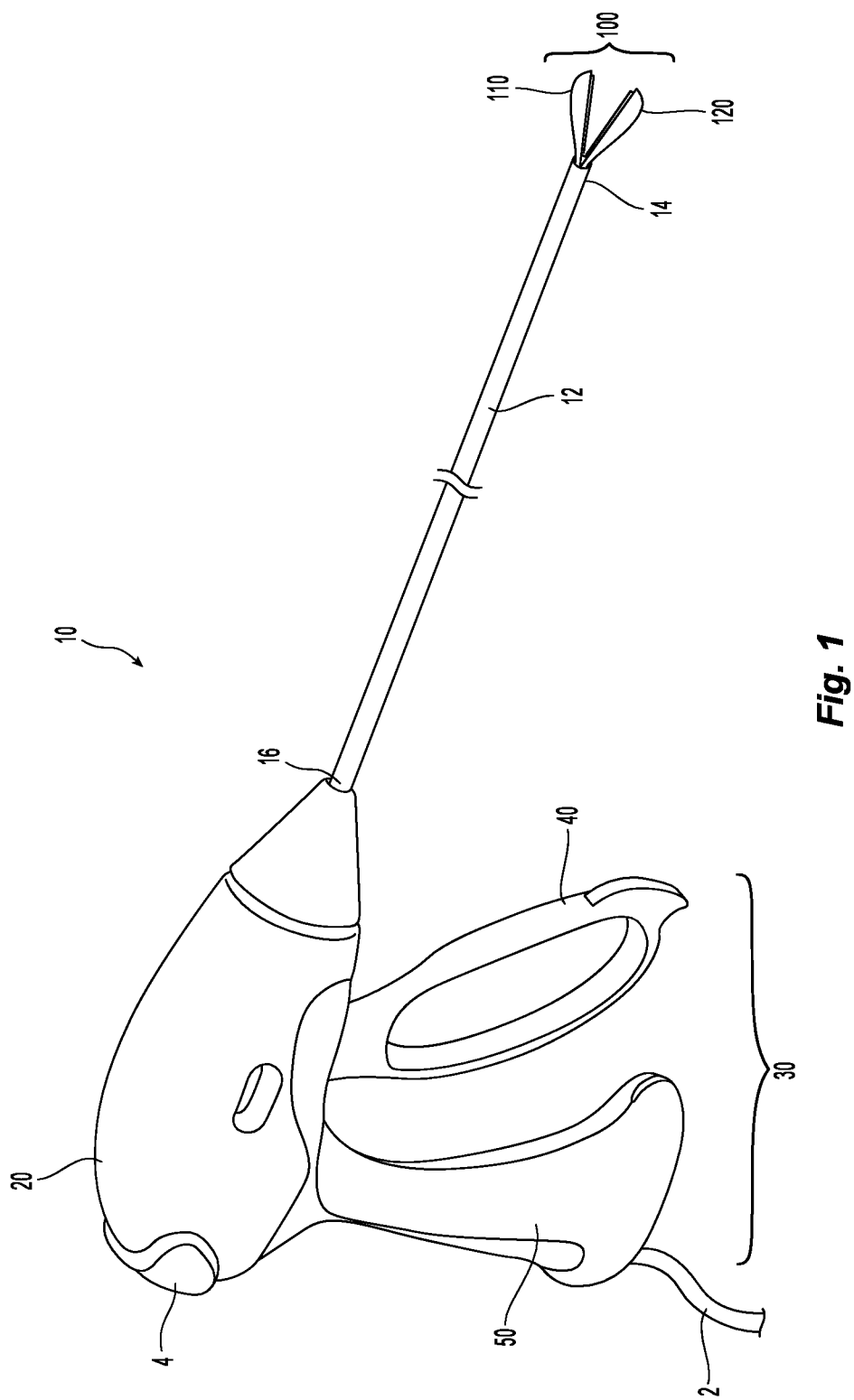
FIG. 1 is a perspective view of an endoscopic surgical forceps provided in accordance with the present disclosure.

Referring to FIG. 1, an embodiment of a surgical forceps provided in accordance with the present disclosure is shown generally identified by reference numeral 10. Although surgical forceps 10 is shown configured for use in connection with endoscopic surgical procedures, the present disclosure is equally applicable for use in more traditional open surgical procedures and with any suitable surgical instrument.

Forceps 10 generally includes a housing 20, a handle assembly 30, an activation switch 4, and an end effector assembly 100. Forceps 10 further includes a shaft 12 having a distal end 14 configured to engage end effector assembly 100 and a proximal end 16 that engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating surfaces 114, 124 of jaw members 110, 120, respectively. Activation switch 4 is coupled between tissue-treating surfaces 114, 124 of jaw members 110, 120, respectively, and the source of energy for enabling the selective supply of energy to jaw members 110, 120 for treating tissue grasped therebetween.

Figure 2:
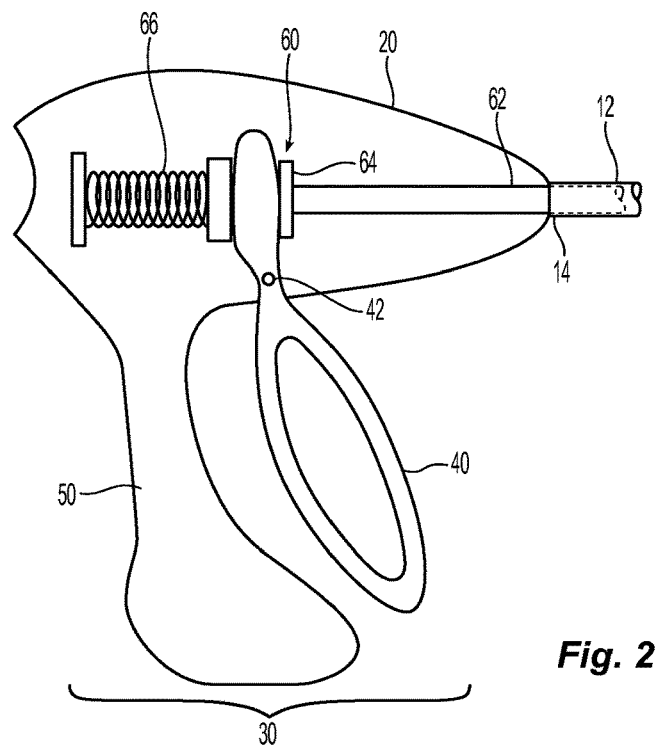
FIG. 2 is a side view of the proximal end of the forceps of FIG. 1, with a portion of the housing removed to enable illustration of the internal features thereof.

With additional reference to FIG. 2, handle assembly 30 includes a fixed handle 50 and a movable handle 40. Fixed handle 50 is integrally associated with housing 20 while movable handle 40 is pivotably coupled to housing 20 within housing 20 via a pivot 42. Movable handle 40 is also operably coupled to a drive assembly 60 operably associated with end effector assembly 100 that, together, mechanically cooperate to impart movement of one or both of jaw members 110, 120 of end effector assembly 100 relative to each other between a spaced-apart position and an approximated position for grasping tissue therebetween. More specifically, movable handle 40 is coupled to a drive bar 62 via a drive mandrel 64 such that movement of movable handle 40 relative to fixed handle 50 effects longitudinal translation of drive bar 62 through shaft 12 and relative to end effector assembly 100. At least the distal end 68 of drive bar 62 defines a hollow configuration that is operably associated with one or both jaw members 110, 120 such that, as detailed below, longitudinal translation of drive bar 62 relative to end effector assembly 100 moves one or both of jaw members 110, 120 between the spaced-apart position and the approximated position.

As shown in FIGS. 1 and 2, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120. A biasing member 66 may be disposed about drive bar 62 and positioned to bias movable handle 40 apart from fixed handle 50. However, other configurations are also contemplated.

Figure 3A:
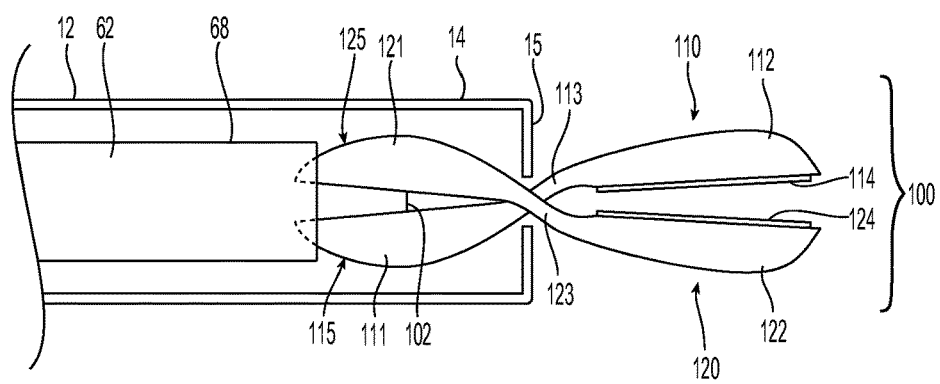
FIG. 3A is a longitudinal, cross-sectional view of the distal end of the forceps of FIG. 1, wherein the jaw members are disposed in a spaced-apart position.
Figure 3B:
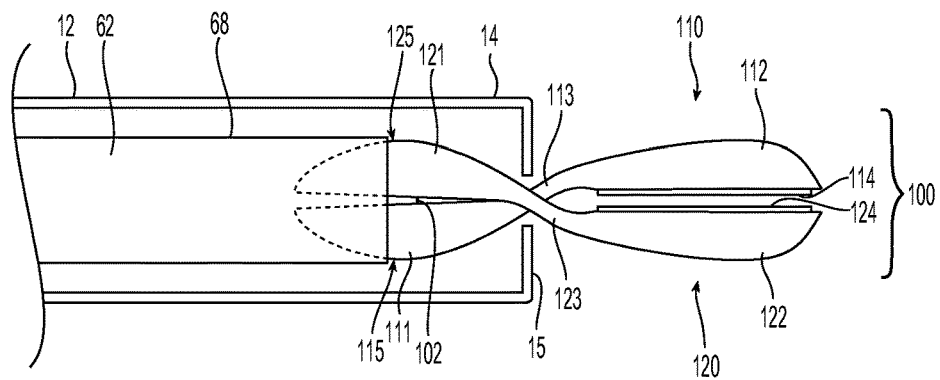
FIG. 3B is a longitudinal, cross-sectional view of the distal end of the forceps of FIG. 1, wherein the jaw members are disposed in an approximated position.

Referring to FIGS. 3A and 3B, in conjunction with FIGS. 1 and 2, end effector assembly 100 includes first and second jaw members 110, 120, each including a proximal portion 111, 121, a distal portion 112, 122, and an intermediate portion 113, 123 extending between and interconnecting the respective proximal and distal portions 111, 121 and 112, 122 of jaw members 110, 120. Proximal portions 111, 121 of jaw members 110, 120, respectively, oppose one another and distal portions 112, 122 of jaw members 110, 120, respectively, oppose one another. Further, jaw members 110, 120 overlap and cross-over one another at intermediate portions 113, 123, respectively, such that the orientation of the opposed proximal portions 111, 121 is opposite that of the opposed distal portions 112, 122.

Proximal portions 111, 121 of jaw members 110, 120, respectively, are retained within distal end 14 of shaft 12 via a retention feature disposed at distal end 14 of shaft 12. More specifically, shaft 12 defines an inwardly-extending, annular flange 15 at distal end 14 thereof that defines a reduced-diameter opening as compared to the inner diameter of shaft 12. This reduced-diameter opening defined by annular flange 15 inhibits the passage of proximal portions 111, 121 of jaw members 110, 120, respectively, distally therethrough, thus retaining proximal portions 111, 121 within distal end 14 of shaft 12. Shaft 12 may alternatively narrow at distal end 14 thereof to define a reduced-diameter opening, or may define any other suitable configuration for this purpose. Proximal portions 111, 121 also define cam surfaces 115, 125 on the outwardly-facing surfaces thereof, the importance of which is detailed below. Hollow distal end 68 of drive bar 62 is at least partially disposed about proximal portions 111, 121 with cam surfaces 115, 125 contacting the inner annular surface of drive bar 62 in operable association therewith, as also detailed below. A biasing member 102 may interconnect proximal portions 111, 121 on the innerfacing surfaces thereof so as to bias proximal portions 111, 121 apart from one another.

Distal portions 112, 122 of jaw members 110, 120, respectively, each define a tissue-treating surface 114, 124, respectively, that is adapted to connect to the source of energy (not shown), e.g., via the wire (or wires) (not shown) extending from cable 2 (FIG. 1) and through shaft 12. Distal portions 112, 122 are movable relative to one another to grasp tissue between tissue-treating surfaces 114, 124. With tissue grasped between tissue-treating surface 114, 124, activation switch 4 (FIG. 1) may be activated to supply energy to either or both tissue-treating surfaces 114, 124 to treat tissue grasped therebetween. Similarly as with proximal portions 111, 121, the inwardly-extending, annular flange 15 at distal end 14 of shaft 12 inhibits the passage of distal portions 112, 122 of jaw members 110, 120, respectively, proximally therethrough. As such, with annular flange 15 interdisposed between proximal and distal portions 111, 121 and 112, 122 of jaw members 110, 120, respectively, end effector assembly 100 is operably retained at distal end 14 of shaft 12.

Intermediate portions 113, 123 of jaw members 110, 120, respectively, define reduced dimensions as compared to proximal and distal portions 111, 121 and 112, 122, respectively, thus enabling intermediate portions 113, 123 to extend through the reduced-diameter opening defined by annular flange 15 of shaft 12. As noted above, jaw members 110, 120 overlap and cross-over one another at intermediate portions 113, 123 thereof. As a result of this configuration, and with end effector assembly 100 operably retained at distal end 14 of shaft 12 via annular flange 15, movement of proximal portions 111, 121 towards one another moves distal portions 112, 122 towards one another, e.g., towards the approximated position of jaw members 110, 120, while movement of proximal portions 111, 121 away from one another moves distal portions 112, 122 away from one another, e.g., towards the spaced-apart position of jaw members 110, 120, without the need for a pivot structure interconnecting jaw members 110, 120. Biasing member 102, noted above, thus biases jaw members 110, 120 towards the spaced-apart position, although other configurations are also contemplated.

Referring still to FIGS. 3A and 3B, in conjunction with FIGS. 1 and 2, initially, movable handle 40 is spaced-apart from fixed handle 50 under the bias of biasing member 66 and, thus, drive bar 62 is disposed in a more-proximal position, wherein hollow distal end 68 of drive bar 62 surrounds only the proximal-most sections of proximal portions 111, 121 of jaw members 110, 120 (see FIG. 3A). As a result of this configuration, proximal portions 111, 1221 are substantially uninhibited, thus permitting biasing member 102 to bias proximal portions 111, 121 apart from one another, corresponding to the spaced-apart position of jaw members 110, 120 (see FIG. 3A).

With jaw members 110, 120 disposed in the spaced-apart position (FIG. 3A), end effector assembly 100 may be manipulated into position such that tissue to be grasped and/or treated is disposed between tissue-treating surfaces 114, 124 of jaw members 110, 120, respectively. Once the desired position of end effector assembly 100 has been achieved, jaw members 110, 120 may be moved to the approximated position to grasp tissue between tissue-treating surfaces 114, 124. In order to move jaw members 110, 120 to the approximated position, movable handle 40 is depressed relative to fixed handle 50 to effect distal translation of drive bar 62 through shaft 12 and relative to end effector assembly 100, e.g., to a more-distal position. This distal translation of drive bar 62 urges hollow distal end 68 of drive bar 62 to further surround proximal portions 111, 121 of jaw members 110, 120. More specifically, upon such distal translation of drive bar 62, the inner annular surface of hollow distal end 68 of drive bar 62 is cammed over cam surfaces 115, 125 of proximal portion 111, 121, thereby urging proximal portions 111, 121 towards one another (see FIG. 3B). As noted above, the urging of proximal portions 111, 121 towards one another moves distal portions 112, 122 towards one another to the approximated position of jaw members 110, 120, wherein tissue is grasped between tissue-treating surfaces 114, 124. Thereafter, activation switch 4 may be activated to initiate the supply of energy to tissue-treating surfaces 114, 124 for treating tissue grasped therebetween.

Once tissue has been treated (or once grasping tissue is no longer required), jaw members 110, 120 may be returned to the spaced-apart position. In order to return jaw members 110, 120 to the spaced-apart position to release the grasped and/or treated tissue, movable handle 40 is released or returned to its initial position, spaced-apart from fixed handle 50, such that drive bar 62 is translated proximally through shaft 12 and relative to end effector assembly 100. Proximal translation of drive bar 62 relative to end effector assembly 100 retracts hollow distal end 68 of drive bar 62 from about proximal portions 111, 121 of jaw members 110, 120, thus permitting biasing member 102 to bias proximal portions 111, 121 apart from one another, thereby urging jaw members 110, 120 back to the spaced-apart position.

Figure 4A:
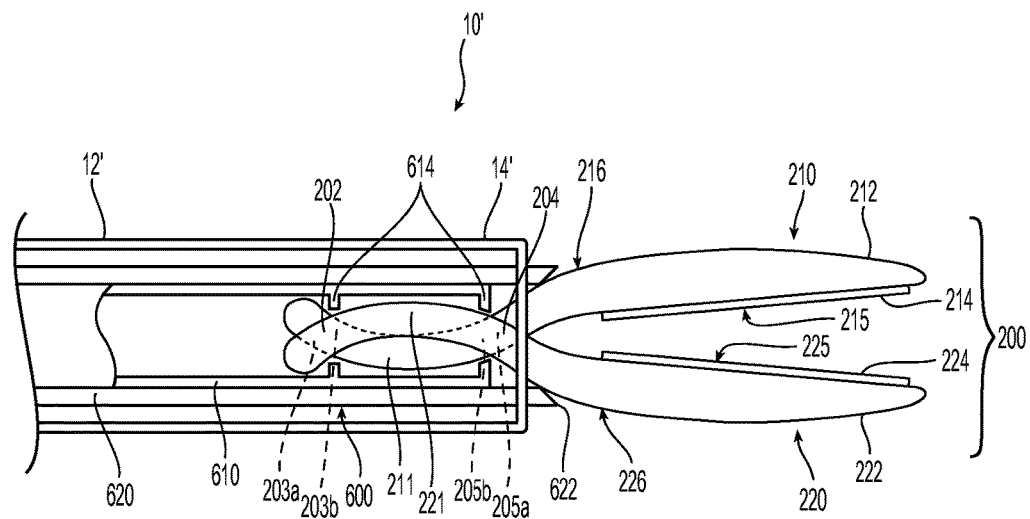
FIG. 4A is a longitudinal, cross-sectional view of the distal end of another forceps similar to the forceps of FIG. 1, wherein the jaw members are disposed in a spaced-apart position.
Figure 4B:
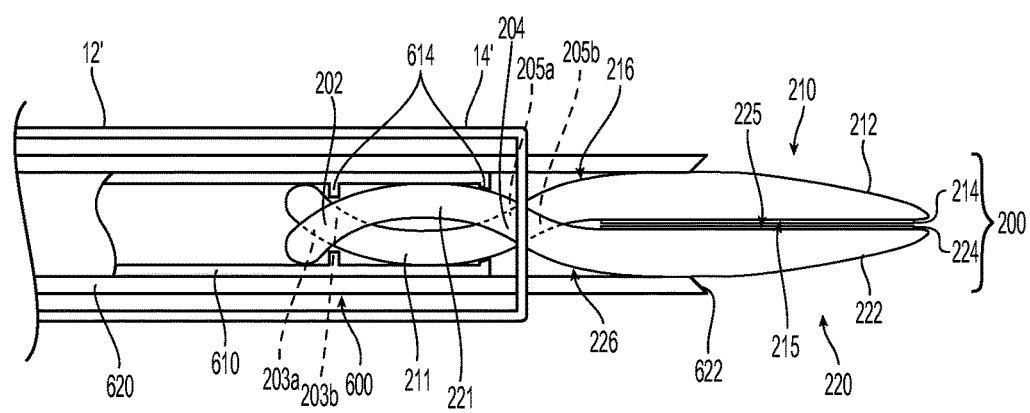
FIG. 4B is a longitudinal, cross-sectional view of the distal end of the forceps of FIG. 4A, wherein the jaw members are disposed in an approximated position.

Turning now to FIGS. 4A and 4B, the distal end of another embodiment of a forceps 10' provide in accordance with the present disclosure is shown generally including an outer shaft 12', and end effector assembly 200 disposed at a distal end 14' of outer shaft 12', and a drive assembly 600 extending through outer shaft 12' and operably associated with end effector assembly 200. Forceps 10' may be configured similarly to and/or include any of the features of forceps 10 (FIGS. 1 and 2), e.g., forceps 10' may include a housing supported at the proximal end of outer shaft 12' similar to housing 20 (FIG. 1) and a handle assembly for selectively actuating drive assembly 600 similar to handle assembly 30 (FIGS. 1 and 2), except as specifically contradicted below.

End effector assembly 200 includes first and second jaw members 210, 220 each including a proximal portion 211, 221 and a distal portion 212, 222. Jaw members 210, 220 are each monolithically formed from a flexible material, e.g., an insulative, biocompatible polymer, although other configurations are also contemplated. Jaw members 210, 220 may be formed from a resilient material so as to bias jaw members 210, 220 towards the spaced-apart position, although other configurations and/or biasing structure are also contemplated. Proximal portions 211, 221 of jaw members 210, 220, respectively, each define arcuate configurations and are oriented oppositely of one another such that the arcuate proximal portions 211, 221 intersect each other at two intersection areas 202, 204. One of the proximal portions 211, 221 defines a recess 203a adjacent the first intersection area 202, while the other proximal portion 211, 221 defines a complementary protrusion 203b adjacent the first intersection area 202. Similarly, one of the proximal portions 211, 221 defines a recess 205a adjacent the second intersection area 204, while the other proximal portion 211, 221 defines a complementary protrusion 205b adjacent the second intersection area 204. Recess 203a, 205a are configured to receive complementary protrusions 203b, 205b, respectively, so as to engage proximal portions 211, 221 of jaw members 210, 220 with one another in an inter-fit manner such that proximal portions 211, 221 are retained in substantially fixed position and orientation relative to one another.

Distal portions 212, 222 of jaw members 210, 220, respectively, defining opposed surfaces having tissue-treating plates 214, 224 disposed thereon. Tissue-treating plates 214, 224 define tissue-treating surfaces 215, 225 configured to grasp tissue therebetween in the approximated position of jaw members 210, 220. Either or both of tissue-treating plates 214, 224 are adapted to connect to the source of energy (not shown) for treating tissue grasped between tissue-treating surfaces 215, 225. Distal portions 212, 222 further define cam surfaces 216, 226 on the outwardly-facing surfaces thereof, the importance of which is detailed below.

Due to the flexible configuration of jaw members 210, 220, despite proximal portions 211, 221 of jaw members 210, 220 being retained in substantially fixed position and orientation relative to one another, flexion of one or both of jaw members 210, 220 intermediate proximal and distal portions 211, 221 and 212, 222, respectively, permits distal portions 212, 222 to move relative to one another between the spaced-apart position of jaw members 210, 220 and the approximated position of jaw members 210, 220 for grasping tissue therebetween. For purposes herein, the term "substantially fixed position and orientation" is meant to allow for some degree of flexion and/or movement of proximal portions 211, 221 that is not the primary cause of jaw members 210, 220 moving between the spaced-apart and approximated positions. Rather, it is the flexion of jaw members 210, 220 that allows for such movement between the spaced-apart and approximated positions. As can be appreciated, this configuration obviates the need for a pivot structure interconnecting jaw members 210, 220.

Drive assembly 600 includes a fixed inner drive bar 610 that is disposed within and fixed relative to outer shaft 12', and a movable outer drive bar 620 that is slidably disposed between fixed inner drive bar 610 and outer shaft 12'. Drive assembly 600 may further include components and/or features similar to those detailed above with respect to drive assembly 60 (FIG. 2) for translating movable outer drive bar 620 about fixed inner drive bar 610 and relative to outer shaft 12' and end effector assembly 200, e.g., upon actuation of a movable handle or other suitable actuator.

At least distal end 612 of fixed inner drive bar 610 is hollow and configured to receive the inter-fit proximal portions 211, 221 of jaw members 210, 220, respectively, of end effector assembly 200. Within hollow distal end 612 of fixed inner drive bar 610 are one or more retention structures, e.g., rings 614 (although other suitable retention structures are also contemplated). Rings 614 are positioned to retain the inter-fit proximal portions 211, 221 of jaw members 210, 220 of end effector assembly 200 within hollow distal end 612 of fixed inner drive bar 610 upon insertion therein. As such, during assembly, proximal portions 211, 221 of jaw members 210, 220, respectively, may first be inter-fit with one another and then inserted into hollow distal end 612 of jaw member 210, 220 under sufficient urging so as to pass at least partially through rings 614 and into position with rings 614 disposed adjacent intersection areas 202, 204, thereby retaining proximal portions 211, 221 of jaw members 210, 220 in substantially fixed position and orientation relative to one another and fixed inner drive bar 610.

Movable outer drive bar 620, as noted above, is slidably disposed between fixed inner drive bar 610 and outer shaft 12' and is coupled to suitable components of drive assembly 600 so as to be selectively translatable about fixed inner drive bar 610 and relative to outer shaft 12' and end effector assembly 200, e.g., upon actuation of a movable handle or other suitable actuator. The distal end of movable outer drive bar 620 may further define a beveled annular edge 622 to facilitate camming about cam surfaces 216, 226 of distal portions 212, 222 of jaw members 210, 220, respectively, as detailed below.

Initially, as shown in FIG. 4A, movable outer drive bar 620 is disposed in a more-proximal position, wherein the beveled annular edge 622 defined at the distal end of movable outer drive bar 620 is spaced proximally from distal portions 212, 222 of jaw members 210, 220, respectively. In this position, distal portions 212, 222 of jaw members 210, 220, respectively, are substantially uninhibited such that jaw members 210, 220 are resiliently (or otherwise) biased towards the spaced-apart position (FIG. 4A).

With jaw members 210, 220 disposed in the spaced-apart position (FIG. 4A), end effector assembly 200 may be manipulated into position as desired, similarly as detailed above. Once the desired position of end effector assembly 200 has been achieved, jaw members 210, 220 may be moved to the approximated position to grasp tissue between tissue-treating surfaces 215, 225. In order to move jaw members 210, 220 to the approximated position, movable outer drive bar 620 is translated distally about fixed inner drive bar 610 and relative to outer shaft 12' and end effector assembly 200, e.g., upon actuation of a movable handle or other suitable actuator. This distal translation of movable outer drive bar 620 urges beveled annular edge 622 of movable outer drive bar 620 to cam about cam surfaces 216, 226 of distal portions 212, 222 of jaw members 210, 220, respectively, thereby urging jaw members 210, 220 to flex such that distal portions 212, 222 are moved towards one another to the approximated position (FIG. 4B) to grasp tissue between tissue-treating surfaces 215, 225.

With tissue grasped between tissue-treating surfaces 215, 225, as shown in FIG. 4B, energy may be supplied to tissue-treating plate 214 and/or tissue-treating plate 224 for treating tissue grasped between tissue-treating surfaces 215, 225. Thereafter, once tissue has been treated (or once grasping tissue is no longer required), jaw members 210, 220 may be returned to the spaced-apart position. In order to return jaw members 210, 220 to the spaced-apart position to release the grasped and/or treated tissue, movable outer drive bar 620 is returned proximally. Proximal translation of movable outer drive bar 620 relative to end effector assembly 200 retracts movable outer drive bar 620 from about distal portions 212, 222 of jaw members 210, 220, thus permitting jaw members 210, 220 to resiliently return to the spaced-apart position (FIG. 4A).

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 5:
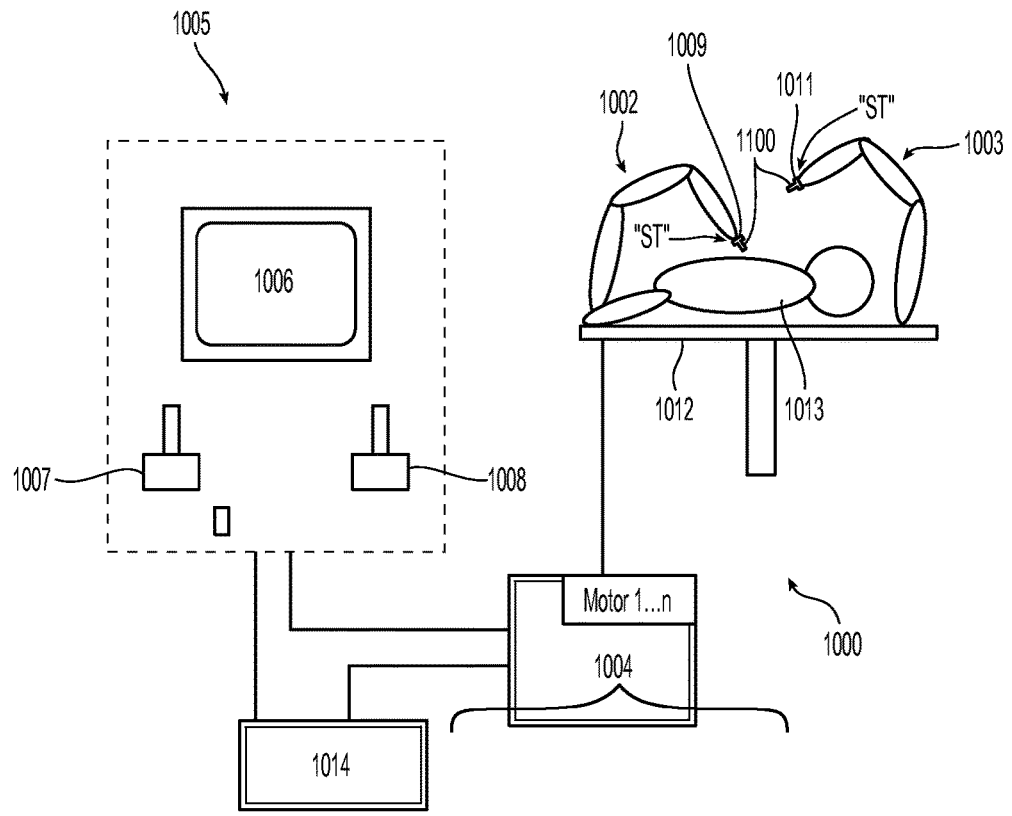
FIG. 5 is a schematic illustration of a robotic surgical system configured for use in conjunction with aspects and features of the present disclosure.

Referring to FIG. 5, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   an end effector assembly including first and second jaw members each defining a proximal portion, a distal portion, and an intermediate portion extending between and interconnecting the respective proximal and distal portions, the distal portions of the first and second jaw members defining tissue-treating surfaces configured to grasp tissue therebetween, the intermediate portions of the first and second jaw members disposed in overlapping relation relative to one another such that a relative orientation of the distal portions of the first and second jaw members is opposite a relative orientation of the proximal portions of the first and second jaw members;
   a shaft defining a proximal end, a distal end, a longitudinal axis extending between the proximal and distal ends, and a distal opening disposed at the distal end and aligned on the longitudinal axis, the shaft configured to receive the proximal portions of the first and second jaw members through the distal opening and into the shaft, the distal portions of the first and second jaw members configured to extend distally from the distal opening of the shaft, the shaft defining a retention feature extending into the distal opening, the retention feature configured to receive the intermediate portions of the first and second jaw members therethrough and inhibit passage of the proximal and distal portions of the first and second jaw members therethrough, thereby operably retaining the first and second jaw members at the distal end of the shaft; and a drive bar disposed within the shaft and operably associated with the proximal portions of the first and second jaw members such that translation of the drive bar through the shaft and relative to the end effector assembly moves the first and second jaw members between a spaced-apart position and an approximated position for grasping tissue between the tissue-treating surfaces thereof, the drive bar disposed about the proximal portion of each of the first and second jaw members.

2. The forceps according to claim 1, wherein the proximal portions of the first and second jaw members define camming surfaces and wherein the drive bar is configured to cam along the camming surfaces to move the first and second jaw members from the spaced-apart position to the approximated position.

3. The forceps according to claim 2, wherein the drive bar includes a hollow distal end defining an interior annular surface, and wherein the drive bar is configured for advancement about the proximal portions of the first and second jaw members such that the interior annular surface cams about the camming surfaces to move the first and second jaw members from the spaced-apart position to the approximated position.

4. The forceps according to claim 1, further including a biasing member disposed between the proximal portions of the first and second jaw members, the biasing member configured to bias the first and second jaw members towards the spaced-apart position.

5. The forceps according to claim 1, wherein the retention feature is an annular flange extending radially inwardly to reduce a diameter of the distal opening, the reduced-diameter distal opening having a diameter greater than that of the intermediate portions of the first and second jaw members and less than that of the proximal and distal portions of the first and second jaw members.

6. The forceps according to claim 1, wherein at least one of the tissue-treating surfaces is adapted to connect to a source or energy for treating tissue grasped therebetween.

7. The forceps according to claim 1, further including a housing supported at the proximal end of the shaft and a handle assembly associated with the housing, the handle assembly including a movable handle coupled to the drive bar, the movable handle selectively actuatable for translating the drive bar through the shaft and relative to the end effector assembly.

8. The forceps according to claim 1, wherein the drive bar is configured to move the proximal portions of the first and second jaw members towards one another to thereby move the first and second jaw members from the spaced-apart position to the approximated position.

* * * * *